United States Patent [19]

Daikuzono

[11] Patent Number: 4,693,244
[45] Date of Patent: Sep. 15, 1987

[54] MEDICAL AND SURGICAL LASER PROBE I

[75] Inventor: Norio Daikuzono, Ichikawa, Japan

[73] Assignee: Surgical Laser Technologies, Inc., Cincinnati, Ohio

[21] Appl. No.: 931,935

[22] Filed: Nov. 17, 1986

Related U.S. Application Data

[63] Continuation of Ser. No. 612,672, May 22, 1984, abandoned.

[51] Int. Cl.[4] ............................................. A61B 17/35
[52] U.S. Cl. ................................... 128/303.1; 128/398
[58] Field of Search ......................................... 128/4–8, 128/303.1, 395–398; 350/96.26; 372/15, 89

[56] References Cited

U.S. PATENT DOCUMENTS

| | | | |
|---|---|---|---|
| 3,123,066 | 3/1964 | Brimley | 128/397 |
| 3,467,098 | 9/1969 | Ayres | 128/303.1 |
| 3,528,424 | 9/1970 | Ayres | 128/303.1 |
| 3,622,743 | 11/1971 | Muncheryan | 128/303.1 |
| 3,821,510 | 6/1974 | Muncheryan | 128/303.1 |
| 3,834,391 | 9/1974 | Block | 128/303.1 |
| 3,865,113 | 2/1975 | Sharon et al. | 128/303.1 |
| 3,865,114 | 2/1975 | Sharon | 128/303.1 |
| 3,906,395 | 9/1975 | Kompa et al. | 372/89 |
| 3,963,347 | 6/1976 | Segre et al. | 372/15 |
| 4,126,136 | 11/1978 | Auth et al. | 128/303.1 |
| 4,185,633 | 1/1980 | Prozorov et al. | 128/303.1 |
| 4,233,493 | 11/1980 | Nath | 219/354 |
| 4,249,533 | 2/1981 | Komiya | 128/303.1 |
| 4,266,547 | 5/1981 | Komiya | 128/303.1 |
| 4,266,549 | 5/1981 | Kimura | 128/303.1 |
| 4,273,109 | 6/1981 | Enderby | 128/303.1 |
| 4,388,924 | 6/1983 | Weissman et al. | 128/303.1 |
| 4,408,602 | 10/1983 | Nakajima | 128/303.1 |
| 4,421,382 | 12/1983 | Doi et al. | 350/96.20 |
| 4,449,528 | 5/1984 | Auth et al. | 128/303.1 |
| 4,454,882 | 6/1984 | Takano | 128/395 |
| 4,469,098 | 9/1984 | Davi | 128/303.1 |
| 4,470,414 | 9/1984 | Imagawa et al. | 128/303.1 |

FOREIGN PATENT DOCUMENTS

| | | | |
|---|---|---|---|
| 0031073 | 7/1981 | European Pat. Off. | 128/6 |
| 0069351 | 1/1983 | European Pat. Off. | 128/303.1 |
| 0105706 | 4/1984 | European Pat. Off. | 128/303.1 |
| 2826383 | 12/1979 | Fed. Rep. of Germany | 128/303.1 |
| 2385372 | 10/1978 | France | 128/6 |
| 2513109 | 9/1981 | France | 128/303.1 |
| 2479485 | 10/1981 | France | 128/303.1 |
| 2023004 | 12/1979 | United Kingdom | 128/303.1 |

OTHER PUBLICATIONS

"Radiation Characteristic of a Tapered Cylindrical Optical Fiber", Change & Auth, J. Opt. Soc. Am., Sep. 1978.

Primary Examiner—Kyle L. Howell
Assistant Examiner—Max F. Hindenberg
Attorney, Agent, or Firm—Jones, Day, Reavis & Pogue

[57] ABSTRACT

A medical and surgical laser probe comprised of a quartz optical fiber and a laser rod member optically connected thereto which is made of an artificial saphire and has a tapered portion so as to emit the incident laser beam from the tip end of the rod member without leaking it out from the tapered face. With this laser probe, laser irradiation in contact with the tissue is enabled and any desired medical and surgical treatment such as incision, coagulation, hemostasis can be attained effectively.

8 Claims, 16 Drawing Figures

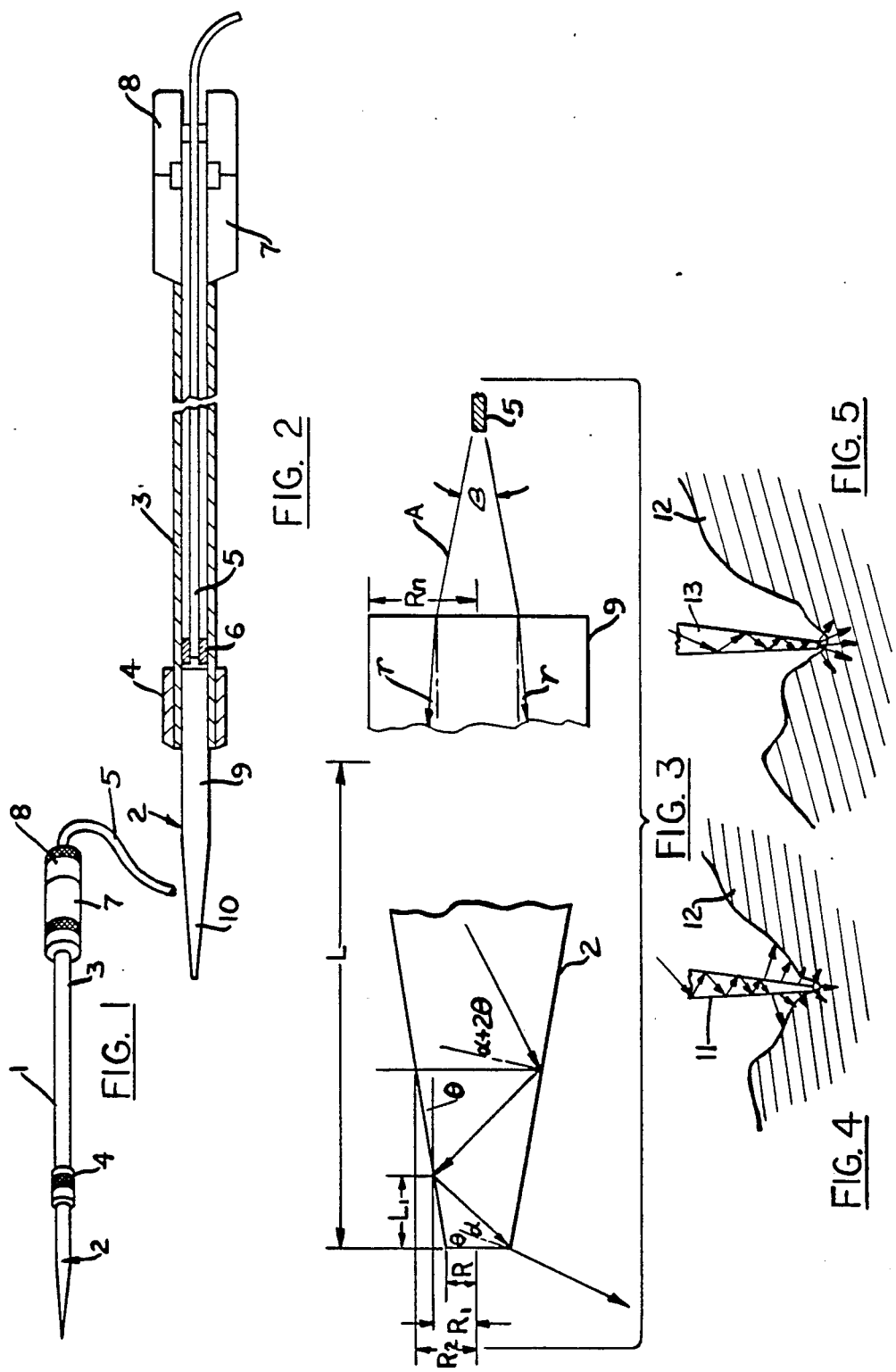

MEDICAL AND SURGICAL LASER PROBE I

This application is a continuation of application Ser. No. 612,672, filed May 22, 1984, now abandonded.

BACKGROUND OF THE INVENTION

1. Field of the Invention

This invention relates to a medical and surgical laser probe and more particularly to a medical and surgical laser probe with a conically tapered rod connected to the tip end of an optical fiber extending from a body of a medical and surgical laser system.

2. Description of Prior Art

Recently, there has been developed and practically used a non-contact type laser irradiation system using an optical fiber for carrying out incision of tissue of a living organism by irradiating laser beam through the optical fiber without contacting the affected part of the tissue. This type of non-contact laser irradiation system effects incision and coagulation by irradiating laser beam such as YAG laser, Ar laser, etc. from the tip end of an elongated quartz core, laser beam guide, made of a single quartz fiber connected optically to a laser source.

Such a non-contact laser irradiation system is rather poor in operating efficiency because it effects the incision without contacting the tissue and without confirming or inspecting the incision condition. This conventional laser irradiation system has another problem that reproducible irradiation effect can not always be obtained. In general, it is required to keep a distance between the tip end of the optical fiber and the tissue to be constant to provide laser beam irradiation of constant energy density. However, in the conventional non-contact laser irradiation system, it is difficult to keep the distance constant, and especially it is difficult to control a distance from the tissue when the system is applied to a laser treatment through an endoscope. In addition, the non-contact irradiation system has such a fatal disadvantage that the laser beam is backscattered from the surface of the tissue and a considerable percentage of the irradiated laser beam energy is lost. In this connection, it is to be noted that when the quartz core is kept in contact with the tissue during the irradiation of laser beam, heat is generated at the contact portion and the end of the quartz core is burnt and broken. Thus, it is not possible to use the conventional laser system in contact with the tissue.

Furthermore, since the divergency angle of laser beam irradiated from the conventional quartz core is as narrow as 7° to 10°, the energy density is not lowered so much even at a position distanced from the irradiation point. Thus, there is caused such an undesirable effect that laser beam of high energy density is irradiated to the tissue around the portion which is being subjected to incision, too, to cause necrosis thereof.

To solve the above-mentioned problems involved in the conventional non-contact laser irradiation system, it may be proposed to provide a quartz rod formed in a tapered shape so as to allow laser beam to leak out from the tapered surface and let laser beam component from the tip end thereof irradiate onto the tissue in contact with the tissue. However, with this quartz rod, the energy density of the laser beam emitted from the tip end of the rod is rather low because of the leakage of laser beam from the tapered surface, so that incision of the tissue cannot be effected with high efficiency.

OBJECT OF THE INVENTION

The invention has been made with a view to solving the problems involved in the conventional laser irradiation system and it is an object of the present invention to provide a medical and surgical laser probe which is capable of effectively gathering laser beam onto the tip end face of a rod member and irradiating the laser beam onto the tissue in contact with the tissue to enable effective incision of the tissue.

SUMMARY OF THE INVENTION

As a result of intensive and extensive study on the requirements for the incision of a tissue, materials of a rod member, conditions for effectively gathering the laser beam, the inventor has achieved the invention which can attain the object as described above.

In accordance with the present invention, there is provided a medical and surgical laser probe having a laser beam transmitting member connected optically to a laser source and a laser beam emitting rod member optically connected to the laser beam transmitting member: which probe is characterized in that said rod member is made of an artificial sapphire and comprised of a laser beam receiving portion and a tapered portion having a laser beam emitting tip end face; and the length and the taper angle of the tapered portion and the radius of the tip end face of the tapered portion are determined so that substantially all laser beam incident on the columnar portion from the laser beam transmitting member is emitted from the tip end face of the tapered portion without leaking out from the tapered face of the tapered portion.

The medical and surgical laser probe of the present invention is capable of being used in contact with the tissue so that the operation efficiency can be improved very much and capable of effecting the incision and coagulation of the tissue without causing any malaffection onto other tissues.

BRIEF DESCRIPTION OF THE DRAWINGS

FIG. 1 is a perspective view of a laser probe according to the present invention;

FIG. 2 is a sectional view of the laser probe of FIG. 1;

FIG. 3 is a diagram showing the propagation of laser beam inside the tapered portion of the laser probe according to the present invention;

FIG. 4 is an explanatory view showing the laser irradiation onto the tissue by a conventional laser irradiation system;

FIG. 5 is a similar explanatory view showing the irradiation of laser beam onto the tissue by the laser probe of the present invention;

PREFERRED EMBODIMENT OF THE INVENTION

Figure 6:
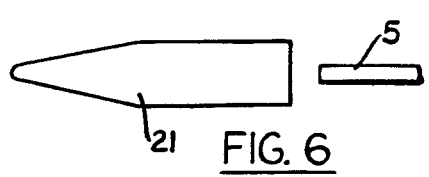
FIGS. 6 to 9 are schematic views of various modifications of the rod members according to the present invention.

Referring now to the drawings, there is illustrated a preferred form of medical and surgical laser probe according to the present invention.

FIG. 1 is a perspective view of a laser probe or laser rod embodying the present invention and FIG. 2 is a sectional view of the same. The laser rod 1 is comprised of a tip rod member 2 and a holder 3. The rod member 2 is fixed to the holder 3 by a fixing coupler 4. An optical fiber extends within the holder 3 and the end thereof, from which the laser beam is emitted, is fixed to the holder 3 by a support 6 in such a manner that the optical axis of the optical fiber 5 and the optical axis of the rod member 2 are aligned with each other. The optical fiber 5 is led to the outside through a holder grip portion 7 and connected to a laser beam source (not shown). The leading-out portion of the fiber 5 is fixed by a fixing member 8 fitted to the holder grip portion 7.

The rod member 2 is made of a single crystal artificial sapphire and comprised, for example, of a columnar portion 9 supported by the holder 3 and a tapered portion 10 having a tip end face from which laser beam is emitted.

The artificial sapphire is formed into the rod member 2 of the present invention in such a manner that the C-axis of the crystalline structure of the artificial sapphire is disposed along the longitudinal direction of the rod member 2. The artificial sapphire of the present invention has characteristics as summarized in the following:

| Material/Formula | $Al_2O_3$ |
|---|---|
| Melting Point | 2030–2050° C. |
| Specific Heat | 0.18(25° C.) |
| Thermal Conductivity, g · cal. · cm$^2$ · sec | 0.0016–0.0034(40° C.) |
| Coefficient of Thermal Expansion, $10^{-7} \times$ cm/°C. | 50–67 |
| Elastic Coefficient, $10^{-6} \times$ kg/cm$^2$ | 5.0 |
| Specific Gravity | 4.0 |
| Hardness (Mohs) | 9 |
| Compressive Strength, kg/cm$^2$ | about 28000 |
| Tensile Strength, kg/cm$^2$ | about 2000 |
| Index of Refraction | 1.76 |
| Absorption Degree of Water | 0.00 |
| Chemical Characteristic | Acid and Base Proof |
| Appearance | Clear |
| Crystal Form | Hexagonal System |
| Transmittance for YAG Laser | 90% or more |

The artificial sapphire of this kind may be obtained by any suitable means such as a zone melting method or Verneuil method. The Verneuil method is advantageous over the zone melting method in respect with light transmission and therefore Verneuil method is preferably employed to manufacture the artificial saphire of the present invention. According to this method, the material, i.e., $Al_2O_3$ powder is subjected to melting at a temperature of about 2040° C. and dropped by gravity through a nozzle to allow crystallization to take place.

The artificial sapphire employed for the rod member 2 has such advantages that it is physiologically neutral, has high mechanical strength, high hardness, high laser beam transmission, excellent thermal resistance and low thermal conductivity and is free from tissue adhesion, which are all required for the material of the rod member of the laser probe. In especial, the thermal conductivity of the artificial sapphire is as low as 1/10 of the thermal conductivity of the quartz which is heretofore used for a conventional laser irradiation system. This feature enables the laser probe to be used in contact with the tissue. Heretofore, there have been no rod member made of an artificial sapphire and therefore the employment of the artificial sapphire rod member constitutes a characteristic feature of the present invention.

The tapered portion of the rod member 2 has such a configuration that the incident laser beam from the fiber 5 is not leaked out from the side of the tapered portion and all emitted from the tip end face of the tapered portion. Such a configuration of the rod member 2 is obtained by adjusting the length of the tapered portion 10, the taper angle and the diameter of the tip end face of the tapered portion 10 so as to satisfy the required conditions.

The conditions will now be described referring to FIG. 3. Referring to FIG. 3, the conditions that a laser beam component A emitted from the quartz laser beam transmitting material, i.e., optical fiber 5 at a divergency angle of $\beta$ is incident on the end face of the columnar portion 9 of the rod member 2 at an incident angle of $\beta/2$, refracted at a refraction angle of $\gamma$, propagated through the rod member 2 and emitted from the verge of the tip end face of the tapered portion 10 after repeated (n times) total reflection, will now be considered. The conditions are critical for emitting all laser beam incident on the rod member 2 only from the tip end face of the tapered portion without leaking out from the tapered face of the portion 10. The taper angle of the tapered portion 10 is now assumed as $\theta$ and the radius of the tip end face is assumed as R and the critical angle for emitting laser beam from the artifical sapphire into air is assumed as $\alpha$. If the radius of the tapered portion 10 at a first reflection point from the emitting end (the last reflection point from the laser receiving end) is $R_1$ and the length from said point to the tip end face is $L_1$, the following equations are obtained:

$$L_1 \tan \theta = R_1 - R_0 \tag{1}$$

$$L_1 \tan (\pi/2 - \alpha - \theta) = R_1 + R_0 \tag{2}$$

If $L_1$ is eliminated from the equations (1) and (2), $R_1$ can be obtained as shown in the following equation (3):

$$R_1 = \frac{\tan (\pi/2 - \alpha - \theta) + \tan \theta}{\tan (\pi/2 - \alpha - \theta) - \tan \theta} R_0 \tag{3}$$

If the radius of the tapered portion 10 at a second reflection point is assumed as $R_2$, the following equation can be obtained similarly.

$$R_1 = \frac{\tan (\pi/2 - \alpha - 3\theta) + \tan \theta}{\tan (\pi/2 - \alpha - 3\theta) - \tan \theta} R_1 \tag{3}$$

Thus, the radius $R_n$ of the tapered portion of the n-th reflection point (the first reflection point from the laser receiving end) can be expressed by:

$$R_n = \frac{\tan [\pi/2 - \alpha - (2n - 1) \theta] + \tan \theta}{\tan [\pi/2 - \alpha - (2n - 1) \theta] - \tan \theta} R_{n-1} \tag{5}$$

If Snell's law is applied to the incidence of laser beam onto the rod member 2 from the optical fiber 5 through air, since the refractive index of the saphire is 1.7 and the refractive index of air is 1.0, the following equation is obtained:

$$1.0 \sin \beta/2 = 1.7 \sin \gamma$$

Therefore, $\gamma = \sin^{-1}(1.0/1.7 \sin \beta/2)$
Since this $\gamma$ is equal to the angle $\pi/2 - \alpha - (2n+1)\theta$ of incidence at the point of n-th reflection, $$\pi/2 - \alpha - (2n+1)\theta = \sin^{-1}(1.0/1.7 \sin \beta/2) \quad (6)$$

$$n = \frac{\pi/2 - \alpha - \sin^{-1}(1.0/1.7 \sin \beta/2) - \theta}{2\theta}$$

The obtained n is substituted for the equation (5) to obtain $R_n$.

On the other hand, the length $L_s$ of the tapered portion from $R_o$ to $R_n$ can be obtained from a right-angled triangle having a base of $L_s$ and a height of $R_n - R_o$. Since $$L_s = \frac{Rn - Ro}{\tan \theta},$$

$R_n$ is substituted for this equation to obtain $L_s$. Since $L_s$ can be considered to be substantially equal to the maximum value of the full length of the tapered portion for satisfying the condition for emitting laser beam only from the tip end face of the tapered portion without leakage of laser beam from the tapered face thereof, the full length L of the tapered portion to meet this condition may satisfy the following expression:

$$L \leq L_s = \frac{Rn - Ro}{\tan \theta} \quad (7)$$

As specific values for satisfying the above formula, there may be mentioned $L \leq 2.72$ mm when $\theta = 10°$ and R=0.2 mm or $L \leq 4.72$ when $\theta = 7°$ and $R_o = 0.2$ mm.

If the rod member has a configuration which cannot satisfy the above condition, laser beam leaks out from the tapered face of a rod member 11 as illustrated in FIG. 4 so that the energy density of laser beam emitted from the tip end face is lowered, which makes the incision of the tissue 12 difficult. In addition, the component of laser beam which leaks out from the taper face irradiates a portion of the tissue distanced from the aimed portion to cause mal-effect thereon.

In contrast, when the configuration of the rod member satisfies the above condition, laser beam is emitted only from the tip end face of a rod member 13 as illustrated in FIG. 5 so that laser beam of high energy density can be obtained to conduct effective incision of the tissue.

The laser beam emitted from the ordinary quartz optical fiber has a divergency angle of as narrow as 7° to 10°, whereas the laser beam emitted from the tip end face of the tapered portion of the rod member of the present invention can have any desired divergency angle, for example, a divergency angle of up to about 100° by adjusting the taper angle. The laser beam having such a wide divergency angle has an extremely high energy density in the vicinity of the tip end face of the tapered portion but the energy density is rapidly lowered as the distance from the end face increases. By this, it is enabled to effect incision of the tissue by laser beam of high energy by contacting the tip end face with the tissue. On the other hand, the energy density of laser beam is low at the area remote from the tip end face so that mal-effect onto the tissue around the contact portion can be minimized. Thus, the laser probe of the present invention enables incision of extremely limited area of the tissue.

The angle of divergency may be selected according to the purpose of laser irradiation. The angle of divergency is preferably selected to be 15° to 40° for coagulation and 40° to 100° for incision. The radius of the tip end face of the rod member may be selected within the range of from 0.01 to 1.5 mm according to the kind of the operation to be conducted.

Although the foregoing description is referred to the rod member with a columnar portion having a radius larger than the radius of the quartz optical fiber and a tapered portion having a diameter continuously reduced from the end thereof and having a planar tip end face as illustrated in FIGS. 1 to 5, the rod member employable for the medical and surgical laser probe of the present invention is not limited to such a configuration and a variety of other configurations may be employed. The modifications of the rod member of the present invention will now be described.

A rod member 21 as illustrated in FIG. 6 has a tip end face of curved surface formed for example by grinding. With this rod member 21, the laser beam emitted from tip end face is once focused at a point near the tip end and then diffused. The so obtained high energy density near the focusing point permits effective incision of the tissue. Further, since the tip end face is formed in a curved shape, convergency of thermal stress near the tip end face is reduced as compared with the planar tip end face and heat resistance can be improved very much. In addition, since the rod member 21 has such a round end face having no angular corner, no entanglement with the tissue is caused during the incision through the contact irradiation of laser beam, and operation can be effected precisely.

Figure 7:
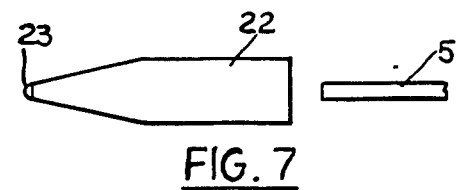

A rod member 22 as illustrated in FIG. 7 has a tip end of the tapered portion which is formed of a melt 23 of an artificial sapphire containing a numerous fine bubble therein. In this rod member 22, the laser beam propagated through the tapered portion is reflected randomly by the bubble in the melt 23 and emitted from the surface of the melt 23. At this time, the energy density on the surface of the melt 23 is very high and the energy density is rapidly decreased as being remoted from the surface so that effective incision of the tissue by contact irradiation of laser beam can be conducted. Further, the divergency angle of the laser beam emitted from the melt 23 is so large that any desired angle of divergency can be obtained by varying the configuration of the melt 23. For example, when the melt is formed in a spherical configuration having a diameter larger than the diameter of the end face of the tapered portion so as to allow emission of laser beam in the backward direction. With this construction, coagulation of the tissue within the organism which cannot be seen directly from the outside can be attained.

To form the melt 23 on the tip end of the tapered portion of the rod member, the tip end portion is first subjected to local heating for example by transmitting laser beam through the rod member while keeping the tip end of the member in abutment with a ceramics material to locally heat the rod member. The locally heated rod member is then rapidly cooled in air. The configuration of the melt 23 is determined mainly by the heating time.

Figure 12:
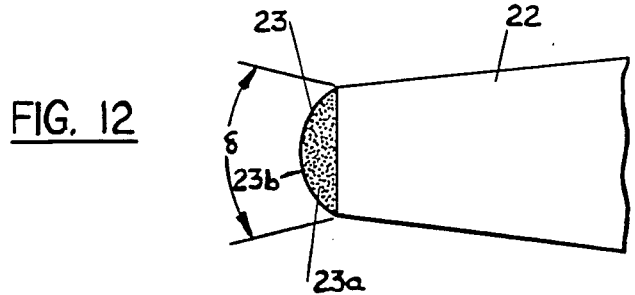
FIG. 12–FIG. 14 are fragmentary enlarged views of the probe tip illustrating various configurations for the bubble melt.
Figure 13:
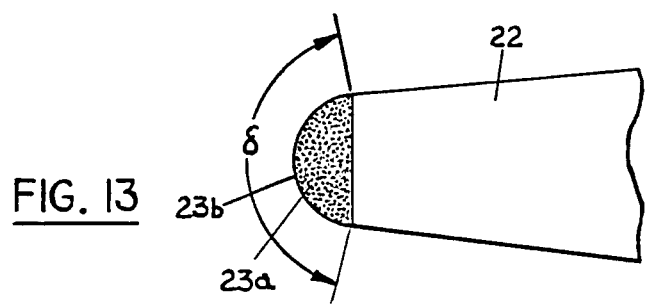
Figure 14:
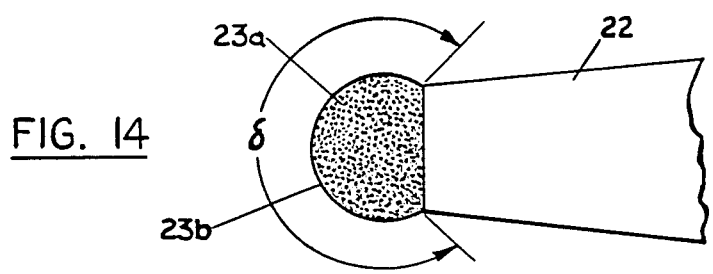

Exemplary configurations for the melt 23 located on the tip end of the tapered portion of the rod member are shown in FIG. 12–FIG. 14. It will be observed that the larger the size of melt 23, the greater the emitting angle δ. In general, it is preferred that the bubbles 23a in the melt be generally uniform in size and uniformly dispersed. Typically, the size of the bubbles will preferably be less then several microns in diameter. Although it is difficult to quantitatively define the rate of porosity of the melt, it is preferred that the melt have a porosity such that it appears translucent with a light transmission of about 20-50%. If the porosity is too large and the light transmission lowered, most of the laser energy will be converted to heat. Furthermore, if the size of the bubbles 23a is too large, the laser beam may be reflected in undesirable directions. Finally, if the bubbles are too large, the structural strength of the melt 23 is lowered.

It should also be observed that the bubbles in the melt should not open on or break through the surface 23b of melt 23. This result can be avoided by forming the melt as described hereinabove.

Figure 8:
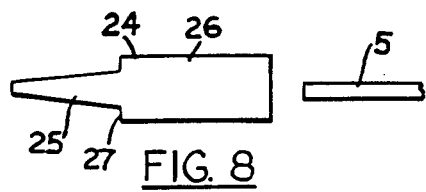
Figure 10:
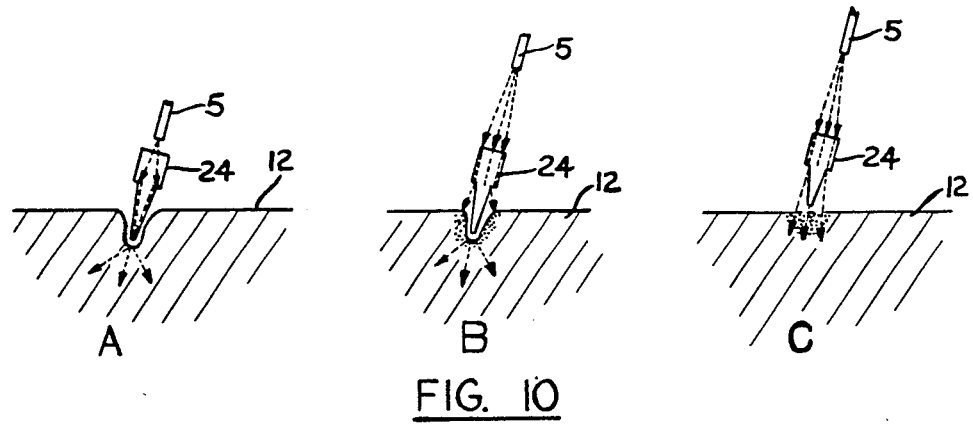
FIGS. 10(a) to (c) are explanatory views showing the laser irradiation onto the tissue by using the rod member as illustrated in FIG. 8.

In a rod member 24 as illustrated in FIG. 8, the diameter of the incidence end of the tapered portion 25 is made smaller than the diameter of the columnar portion 26 for example by grinding so that the columnar portion 26b has an annular end face 27 on the end adjacent to the tapered portion 25. This shape of the rod member 24 provides various usage as shown in FIG. 10 by varying the point of incidence of laser beam, i.e. the distance from the quartz optical fiber 5. Stated illustratively, when the distance from the optical fiber 5 is short as shown in FIG. 10(a), laser beam is not emitted from the annular end face 27 of the columnar portion 26 so that only the incision of the tissue 12 is carried out by laser beam emitted from the tapered portion 25. When the distance from the optical fiber 5 is longer so as to allow laser beam to be incident all over the incident face of the columnar porton 26 as shown in FIG. 10(b), laser beam is emitted also from the annular end face 27 of the columnar portion 26. This component of laser beam can be used for coagulation of the tissue 12. Thus, the incision and coagulation can be effected simultaneously. Further, as shown in FIG. 10(c), only the coagulation of the tissue 12 can be carried out by non-contact irradiation of laser beam.

Figure 9:
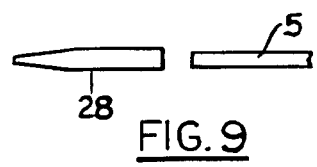
Figure 11:
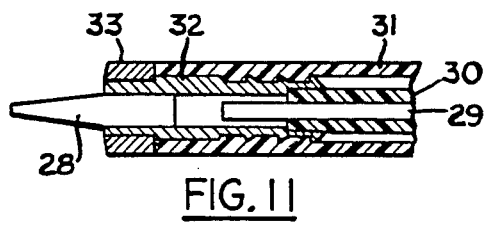
FIG. 11 is a sectional view of the mounting structure of the rod member as illustrated in FIG. 9.

A rod member 28 as shown in FIG. 9 has a similar configuration to that as illustrated in FIGS. 1 to 5 but has a diameter smaller than an outer tube 31 of an optical fiber 29 as shown in FIG. 11 and has a length as short as 7 mm. This rod member 28 is mounted on the tip end of the outer tube 31 of the optical fiber 29 and used for a biopsy channel such as endoscopic biopsy. The outer tube 31 is made for example of Teflon (a trade name of polymer of tetrafluoroethylene manufactured and sold by du Pont) and is formed with an inner thread at the tip end portion thereof. A mounting member 32 having outer threads at the forward and rearward portions thereof is meshed with the tube 31 and the columnar portion of the rod member 28 is inserted into the mounting member 32 and a socket 33 having an inner thread on the inside thereof is meshed with the rear portion of the mounting member 32. Thus, the rod member 28 is mounted. With this rod member 28, hemostasis and incision through the endoscope can be carried out.

As described above, the columnar portion 9 is formed for the purpose of fixing the rod member 2 to the holder 3 and therefore it may be omitted so that the rod member may be formed substantially in a tapered shape as a whole if an appropriate fixing means is provided. In other words, it suffices that the rod member has a tapered shape at its portion forward of the first reflection point from the incidence end of laser beam, and the configuration of its portion rearward of said point is not critical. Thus, the rod member may have a configuration which does not obstruct the light path of laser beam to the tapered portion.

EXAMPLE

A brain tumor of a human being was removed by using a laser probe having a configuration as illustrated in FIG. 2 in contact with the tissue. The rod member of the laser probe has a radius of the laser emitting end face of 0.3 mm, a diameter of the columnar portion of 3 mm, a length of the columnar portion of 10 mm and a total length of the rod member of 50 mm. An optical fiber is so disposed that the tip end of the fiber is spaced by 2 mm from the rear face of the rod member and the angle β of divergency from the optical fiber is selected to be 8°.

For Comparative Example, a conventional laser irradiation system having a quartz core whose diameter is 0.6 mm was used without being in contact with the tissue, keeping a distance of 1 mm from the tissue.

In Example and Comparative Example, Nd:YAG laser beam having a wave length of 1.06 μm was used and the output was 50W. The result shows that necrosis of 2 mm in thickness was observed in Comparative Example, while the thickness of the necrosis was reduced to 0.6 mm in Example of the present invention. In addition, damage of the tissue around the tumor was minimized in Example as compared with the method of Comparative Example.

I claim:

1. A medical and surgical laser probe for contact laser surgery; the probe optically connected to a laser source through an optical laser guide means; which probe is characterized in that the probe is made of an optically transparent solid material and comprised of a laser beam receiving portion and a tapered portion having a laser beam emitting tip end face; the tapered portion defining cross-sections of generally circular form having no surgical cutting edges along the tapered length thereof, and the length and the taper angle of the tapered portion and the radius of the tip end face of the tapered portion are determined and structural so that substantially all laser beam incident on the laser beam receiving portion from the laser beam guide means is emitted from the tip end face of the tapered portion without leaking out from the tapered face of the tapered portion; the laser beam being concentrated at the tip end face whereby said concentrated laser beam facilitates the surgical cutting of tissue.

2. A medical and surgical laser probe as claimed in claim 1, wherein the length L and the taper θ of the tapered portion and the radius Ro of the tip end face of the tapered portion are values which satisfy the following inequality.

$$L \leq \frac{Rn - Ro}{\tan \theta} \tag{5}$$

$$Rn = \frac{\tan[\pi/2 - \alpha - (2n - 1)\theta] + \tan \theta}{\tan[\pi/2 - \alpha - (2n - 1)\theta] - \tan \theta} Rn - 1$$

$$n = \frac{\pi/2 - \alpha - \sin^{-1}(1.0/1.7 \sin \beta/2) - \theta}{2\theta} \quad (6)$$

where $\alpha$ is a critical angle of the artifical sapphire and $\beta$ is an emitting angle of the laser transmitting member.

3. A medical and surgical laser probe as claimed in claim 1, wherein said tip end face has a curved surface.

4. A medical and surgical laser probe as claimed in claim 1 wherein the tip end of the tapered portion has a melt of artificial sapphire which contains a numerous fine bubble therein.

5. A medical and surgical laser probe as claimed in claim 1 wherein the diameter of the tapered portion of the side of incidence is smaller than the diameter of said laser beam receiving portion so that said portion has an annular end face on the side confronting the tapered portion.

6. A medical and surgical laser probe as claimed in claim 2, wherein said tip end face has a curved surface.

7. A medical and surgical laser probe as claimed in claim 2 wherein the tip end of the tapered portion has a melt of artificial sapphire which contains a numerous fine bubble therein.

8. A medical and surgical laser probe as claimed in claim 2 wherein the diameter of the tapered portion on the side of incidence is smaller than the diameter of said laser beam receiving portion so that said portion has an annular end face on the side confronting the tapered portion.

* * * * *